United States Patent [19]

Neubauer

[11] Patent Number: 4,677,990
[45] Date of Patent: Jul. 7, 1987

[54] ENDOCARDIAL ELECTRODE CONTROLLABLE TO FORM SELECTED CONTOURS

[75] Inventor: Heinz Neubauer, Jaerfaella, Sweden

[73] Assignee: Siemens Aktiengesellschaft, Berlin and Munich, Fed. Rep. of Germany

[21] Appl. No.: 832,677

[22] Filed: Feb. 25, 1986

[30] Foreign Application Priority Data

Feb. 28, 1985 [DE] Fed. Rep. of Germany ....... 3507119

[51] Int. Cl.⁴ .............................................. A61N 1/05
[52] U.S. Cl. ................................ 128/786; 128/419 P
[58] Field of Search ................................ 128/784–786, 128/419 P, 642, 772; 604/95

[56] References Cited

U.S. PATENT DOCUMENTS 3,470,876 10/1969 Barchilon ............................ 128/348
4,136,703 1/1979 Wittkampf ....................... 128/419 P
4,350,169 9/1982 Dutcher .............................. 128/783

FOREIGN PATENT DOCUMENTS 216843 7/1908 Fed. Rep. of Germany.
2149449 4/1972 Fed. Rep. of Germany.
2516848 10/1976 Fed. Rep. of Germany.
990417 9/1951 France.
43-27685 11/1968 Japan ..................................... 604/95
2064963 6/1981 United Kingdom.
929112 5/1982 U.S.S.R. .............................. 128/785

*Primary Examiner*—Lee S. Cohen
*Attorney, Agent, or Firm*—Hill, Van Santen, Steadman & Simpson

[57] ABSTRACT

An endocardial electrode controllable to form selected contours has a flexible electrical conductor with an internal axial channel and covered with an insulating sheath. A traction element extends through the channel and is freely moveable therein and is attached to the conductor at a selected location. A portion of the traction element is guided outside of the conductor but within the insulating sheath, and the traction element projects from the channel at a proximal end of the electrode. Tension exerted on the tension element at the proximal end deforms the conductor to a selected contour dependent upon the amount of tension.

8 Claims, 4 Drawing Figures

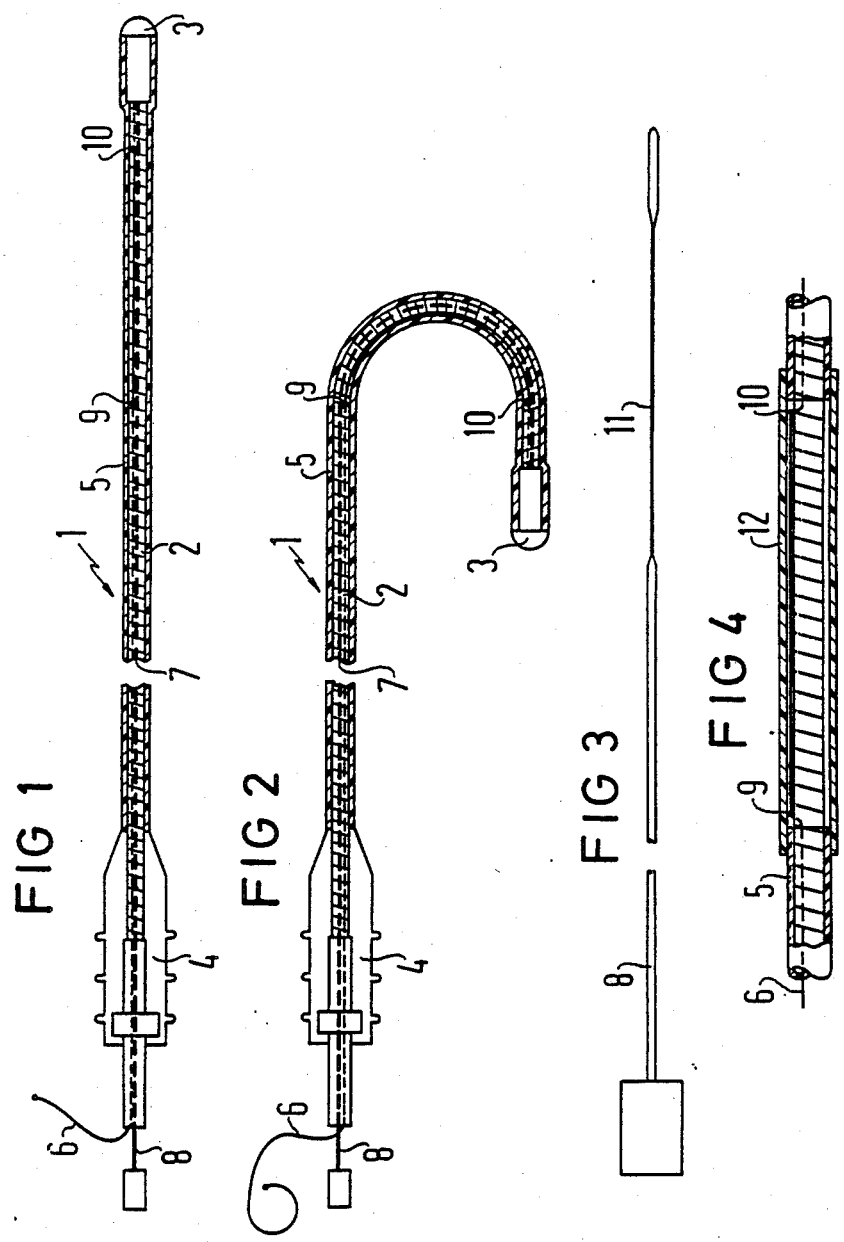

4,677,990

ENDOCARDIAL ELECTRODE CONTROLLABLE TO FORM SELECTED CONTOURS

BACKGROUND OF THE INVENTION

1. Field of the Invention

The present invention relates to endocardial electrodes for intra-cardial stimulation of the heart and/or for sensing heart signals.

2. Description of the Prior Art

Endocardial electrodes for stimulating and/or sensing signals from heart tissue are known in the art, generally consisting of an elongated flexible electrical conductor externally covered by an insulating sheath and having an internal channel for the introduction of a mandrin. Such electrodes have at least one electrode head for contact with the heart tissue disposed at the distal end of the conductor.

When implanting endocardial electrodes, for example in the atrium or at some other location to which access is difficult, it is frequently necessary that the electrode line be curved in certain regions. An electrode having a curved J-shape for stimulating the atrium, for example is known from U.S. Pat. No. 4,402,328. This electrode is permanently pre-shaped. For introduction through a vein, such electrodes are first stretched so as to be substantially straight by means of a mandrin, and the distal end of the electrode assumes the intended curvature when the mandrin is retracted.

Another possibility for inserting electrodes at locations to which access is difficult, is the use of specially pre-shaped mandrins. Whether the electrode or the mandrin is pre-shaped, the curvature of the electrode cannot be modified once the electrode has been placed in the heart, or during introduction of the electrode to the heart. With the use of a mandrin, variations within certain limits can be achieved by having mandrins of different shapes available. For this purpose, however, it is necessary to completely withdraw the mandrin from the electrode and either re-introduce the same mandrin after changing the shape thereof, or replacing one mandrin with a different mandrin having a different contour.

In conventional electrode structures, a further disadvantage exists in that the shape of the pre-formed electrode may not be optimum for every heart and for every type of use. Moreover, an electrode line which is not pre-shaped, but is instead bent by special mandrins, does not remain in this desired shape without undertaking further steps after the mandrin has been withdrawn.

SUMMARY OF THE INVENTION

It is an object of the present invention to provide an endocardial electrode structure which can assume arbitrary curvatures or contours with infinite variation in defined regions of the electrode line during implantation, and can be reliably retained in the desired shape at the end of the implantation.

The above object is inventively achieved in an endocardial electrode having an elongated traction element freely moveable in the longitudinal direction in the interior channel formed in the electrode conductor. The traction element is rigidly connected to the electrode at a selected location along the length thereof, and is guided outside of the channel, but still within the insulating sheath, over a selected distance. Said element is projecting from the channel at the proximal end of the electrode. The traction element is centrally guided in the majority of the electrode and is eccentricaly guided only in the defined selected region. The traction element is accessible at the proximal end of the electrode and is pulled to exert tension thereon during implantation. This tension causes a curvature of the electrical conductor, and therefore of the electrode, in the defined region over which the traction element is eccentrically guided. Depending upon the degree of tension, the curvature can be selected with infinite variation from a substantially straight electrode conductor to an electrode conductor which is bent nearly circular. The degree of bending is proportional to the force exerted on the traction element.

The traction element is preferably rigidly connected to the electrode near the distal end thereof. In the simplest embodiment, the traction element may be directly connected to the electrode head attached at the distal end. The region over which the traction element is eccentrically guided will generally be disposed in proximity to the distal end. This does not exclude, however, selecting the eccentrically guided region at other locations along the electrical conductor. It is within the scope of the subject matter described herein to provide a plurality of regions along the electrode over which the traction element is eccentrically guided, in order to simultaneously produce different curvatures at different locations of the conductor. It is also within the framework of the subject matter disclosed herein to provide a plurality of traction elements which are eccentrically guided at different regions in order to again produce different curvatures of the electrical conductor at different times.

A thread having very low elasticity may function as the traction element. Such a thread is guided in the channel and is conducted through the electrical conductor until the point which begins the region which is to be bent. At this point, the thread exits the conductor through any suitable opening and proceeds parallel to the conductor outside thereof, but within the insulating sheath, and is re-introduced to the conductor channel through another suitable opening at the end of the region which is to be bent. The thread preferably occupies sufficiently little space within the channel so that introduction of a mandrin is not impeded. In order to facilitate longitudinal mobility of the traction element, in a further embodiment of the invention the insulating sheath surrounding the electrical conductor has a slightly larger inside diameter in the region over which the traction element is eccentrically guided, i.e., the region to be bent. The insulating sheath along this region loosely surrounds the electrical conductor and leaves sufficient latitude for the thread or some other traction element to move therein.

In another embodiment of the invention, the mandrin has a selected profile in that region of the mandrin which coincides, when the mandrin is fully introduced into the electrode, with the region over which the traction element is eccentrically guided. In a preferred embodiment, the mandrin in this region is reduced in cross section in order to reduce the tractive force required for bending the electrical conductor when the mandrin is introduced.

By use of the traction element as described herein, it is possible to create any type of electrode arrangement, which may be employed as a standard ventricle electrode or as a special atrium electrode. Moreover, implanting of the electrode is substantially simplified by the ability to continuously vary the contour of the electrode, because an optimum bend can quickly be set. If, for example, the electrode arrangement is to be anchored with a J-shaped hook in the atrium, the traction element can be rigidly connected to the conductor at the extreme proximal end, and the conductor introduced substantially straight and tension exerted after insertion so as to achieve the desired J-shape. The proximal end of the traction element can then be fixed so that the J-shape is permanently retained.

DESCRIPTION OF THE DRAWING

FIG. 1 is a side sectional view of an electrode arrangement constructed in accordance with the principles of the present invention with no tension exerted thereon.

FIG. 2 is a side sectional view of the electrode arrangement of FIG. 1 with tension exerted on the traction element.

FIG. 3 is a side view of a mandrin for use in the electrode arrangement of FIG. 1.

FIG. 4 is an enlarged side sectional view of a portion of a further embodiment of an electrode constructed in accordance with the principles of the present invention.

DESCRIPTION OF THE PREFERRED EMBODIMENTS

A unipolar electrode constructed in accordance with the principles of the present invention is shown in FIG. 1 generally referenced at 1. The electrode 1 has a helically wound electrical conductor 2 of tape material which is connected at a distal end to an electrode head 3 and at a proximal end to a terminal 4 adapted for connection to a heart pacemaker (not shown). The electrical conductor 2 is surrounded by an insulating sheath 5 over its full length. The electrode 1 has a channel 7 inside the electrical conductor 2 permitting introduction of a mandrin 8. The subject matter disclosed herein is not, however, limited to electrodes specifically of the type shown in FIG. 1, and has equal utility multi-pole electrodes and in electrodes with electrical conductors other than wound tape conductors. For example, the electrical conductor may be wire-like and may be coaxially or multi-filament wound for multi-pole lines.

The electrode 1 is provided with traction element 6 which may be, for example, a substantially non-stretchable thread. The traction element 6 is guided in the channel 7 along the majority thereof within the electrical conductor 2, and extends through the electrical conductor 2 to the exterior thereof at a location 9, and thereafter proceeds outside of the conductor 2 parallel thereto between the electrical conductor 2 and the insulating sheath 5 to a further location 10. At the location 10, the traction element 6 again proceeds through the electrical conductor 2 into the channel 7, and is again centrally guided within the channel 7 to the electrode head 3, where the traction element 6 is rigidly attached. Alternatively, the traction element 6 may be attached in the region of the location 10, and it is then not necessary to again conduct the traction element 6 through the electrical conductor 2.

If, as in the exemplary embodiment shown in FIG. 1, a mandrin 8 is introduced to the distal end of the electrode 1, a contour in the region of the electrical conductor 2 between the locations 9 and 10 can be selected with any desired curvature by pulling the traction element 6 at the proximal end of the electrode 1. The curvature can subsequently be cancelled by releasing the tension. A continuously variable bending of the electrical conductor 2 in this region is, thus, possible during implantation in a simple manner, thereby significantly simplifying guidance of the electrode 1 into the heart and, thus, accelerating the implantation procedure.

The same electrode is shown in FIG. 2 as in FIG. 1, but with a curved electrical conductor 2 caused by tension on the traction element 6 at the proximal end. If a specific curvature is to be retained after implantation, the traction element 6 is rigidly connected to the electrode 1 at the proximal end with a selected tension. The established curvature is thereby fixed.

It is also possible to eccentrically guide the traction element not only at a single region, but also at a plurality of regions along the length of the electrode 1, and thereby achieve a curvature in different regions of the electrical conductor 2. It is also possible to utilize a plurality of traction elements 6 eccentrically guided at different regions, so as to bend different portions of the electrode 1 at different times during implantation.

When tension is exerted on the traction element 6, the electrical conductor 2, and, thus, the electrode 1, initially curves only in one direction, i.e., toward that side of the electrode 1 at which the traction element 6 is eccentrically guided. With the assistance of the mandrin 8 as shown in FIG. 3, however, the electrode 1 can be rotated so that the distal end of the electrode assumes any desired radial position. In order to assist such manipulation, the mandrin 8 has a selected profile, such as a diminished cross section in a region 11, coinciding with the eccentrically guided region of the traction element 6, in order to facilitate bending of the electrode 1.

A portion of a further embodiment of an electrode arrangement in accordance with the principles of the present invention is shown in FIG. 4. In order to achieve a larger inside diameter of the insulating sheath in the eccentrically guided region, the standard insulating sheath 5 is interrupted at this region, and an insulating sheath 12 having a larger inside diameter is slipped over this region. The enlarged sheath 12 is sealed at each end thereof to the standard sheath 5.

Although modifications and changes may be suggested by those skilled in the art it is the intention of the inventor to embody within the patent warranted hereon all changes and modifications as reasonably and properly come within the scope of his contribution to the art.

I claim as my invention:

1. An endocardial electrode controllable to form selected contours comprising:
    a flexible electrical conductor having an internal axial channel and covered with an insulating sheath, said conductor having a distal end and a proximal end;
    at least one electrode head attached at said distal end of said conductor for contact with heart tissue; and
    at least one traction element extending through and freely movable in said channel and attached to said conductor at a selected location and having at least one portion thereof eccentrically guided outside and parallel to said conductor within said insulating sheath for a predetermined distance, said traction element projecting from said channel at said proximal end thereof;
    whereby tension exerted on said traction element at said proximal end deforms said conductor in a region substantially co-extensive with said portion of said traction element to a selected contour dependent upon the amount of tension.

2. An endocardial electrode as claimed in claim 1, wherein said traction element is attached to said conductor in proximity to said distal end.

3. An endocardial electrode as claimed in claim 1, wherein said insulating sheath has a larger inside diameter coextensive with each portion of said traction element guided outside said conductor.

4. An endocardial electrode as claimed in claim 3, wherein said insulating sheath is interrupted coextensive with each said portion of said traction element guided outside said conductor and further comprising a section of enlarged insulating sheath extending over each portion and sealed at each end to said interrupted insulating sheath.

5. An endocardial electrode as claimed in claim 1, wherein said traction element is substantially non-stretchable thread.

6. An endocardial electrode as claimed in claim 1, further comprising a mandrin received in said channel.

7. An endocardial electrode as claimed in claim 6, wherein said mandrin has a selected profile coextensive, when said mandrin is completely received in said channel, with said portion of said traction element guided outside said conductor.

8. An endocardial electrode as claimed in claim 7, wherein said profile is a region of reduced cross section.

* * * * *